US012484896B2

(12) United States Patent
Nawrocki et al.

(10) Patent No.: US 12,484,896 B2
(45) Date of Patent: Dec. 2, 2025

(54) BARBED SUTURES HAVING CONTOURED BARBS THAT FACILITATE PASSAGE THROUGH TISSUE AND INCREASE HOLDING STRENGTH

(71) Applicant: Cilag GMBH International, Zug (CH)

(72) Inventors: Jesse G. Nawrocki, Annandale, NJ (US); Jason T. Perkins, Easton, PA (US); David C. Lindh, Sr., Flemington, NJ (US)

(73) Assignee: Cilag GmbH International, Zug (CH)

( * ) Notice: Subject to any disclaimer, the term of this patent is extended or adjusted under 35 U.S.C. 154(b) by 280 days.

(21) Appl. No.: 18/310,811

(22) Filed: May 2, 2023

(65) Prior Publication Data

US 2023/0263519 A1 Aug. 24, 2023

Related U.S. Application Data

(63) Continuation of application No. 13/621,625, filed on Sep. 17, 2012, now Pat. No. 11,672,529.

(51) Int. Cl.
*A61B 17/06* (2006.01)
*A61B 17/04* (2006.01)

(52) U.S. Cl.
CPC *A61B 17/06166* (2013.01); *A61B 2017/0417* (2013.01); *A61B 2017/0464* (2013.01); *A61B 2017/06176* (2013.01)

(58) Field of Classification Search
CPC .... A61B 17/06166; A61B 2017/06176; A61B 2017/06057; A61B 17/06; A61B 2017/06052
See application file for complete search history.

(56) References Cited

U.S. PATENT DOCUMENTS 3,123,913 A 3/1964 Rubin
5,053,047 A 10/1991 Yoon
(Continued)

FOREIGN PATENT DOCUMENTS

EP 1857236 B1 11/2009
EP 1858243 B1 11/2009
(Continued)

OTHER PUBLICATIONS

Extended European Search Report received for European Application No. 18185410.0, mailed on Nov. 9, 2018, 9 pages.
(Continued)

*Primary Examiner* — Katherine Shi
(74) *Attorney, Agent, or Firm* — Amir Bishara

(57) ABSTRACT

A wound closure device includes a filamentary element having a proximal end and a distal end, and a plurality of barbs extending outwardly from the filamentary element. Each barb has a base connected with the filamentary element, a tip spaced from the base, and an outer edge that extends between the base and the tip. The outer edge includes a first section having a concave surface that extends between the base and a transition point of the barb and a second section having a convex surface that extends between the transition point of the barb and the tip of the barb. The outer edge transforms from the concave surface of the first section to the convex curve of the second section at the transition point of the barb. The tip of the barb has a convexly curved surface facing the distal end of the filamentary element. The unique dual radius shape of the outer edge of the barbs and the tips of the barbs minimizes resistance when the filamentary element is pulled in a first direction through tissue and maximizes resistance to movement when the filamentary element is pulled in an opposite,
(Continued)

second direction through tissue for holding the wound closure device stationary.

15 Claims, 7 Drawing Sheets

(56) References Cited

U.S. PATENT DOCUMENTS

| | | | |
|---|---|---|---|
| 5,123,913 | A | 6/1992 | Wilk et al. |
| 5,222,976 | A | 6/1993 | Yoon |
| 5,312,436 | A | 5/1994 | Coffey et al. |
| 5,403,346 | A | 4/1995 | Loeser |
| 5,450,860 | A | 9/1995 | Oconnor |
| 5,683,417 | A | 11/1997 | Cooper |
| 5,697,950 | A | 12/1997 | Fucci et al. |
| 5,707,394 | A | 1/1998 | Miller et al. |
| 5,803,903 | A | 9/1998 | Athas et al. |
| 6,033,430 | A | 3/2000 | Bonutti |
| 6,050,998 | A | 4/2000 | Fletcher |
| 6,117,139 | A | 9/2000 | Shino |
| RE36,974 | E | 11/2000 | Bonutti |
| 6,241,747 | B1 | 6/2001 | Ruff |
| 6,264,675 | B1 | 7/2001 | Brotz |
| 6,319,263 | B1 | 11/2001 | Levinson |
| 6,577,310 | B1 | 6/2003 | Kim et al. |
| 6,730,112 | B2 | 5/2004 | Levinson |
| 6,875,214 | B2 | 4/2005 | Supinski |
| 7,468,068 | B2 | 12/2008 | Kolster |
| 7,731,732 | B2 | 6/2010 | Ken |
| 7,850,700 | B2 | 12/2010 | Sakura |
| 7,850,894 | B2 | 12/2010 | Lindh, Sr. et al. |
| 8,142,513 | B2 | 3/2012 | Shalon et al. |
| 8,267,961 | B2 | 9/2012 | Popadiuk et al. |
| 8,715,320 | B2 | 5/2014 | Lindh, Sr. |
| 8,721,681 | B2 | 5/2014 | Ruff et al. |
| 10,582,926 | B2 | 3/2020 | Nawrocki et al. |
| 10,973,513 | B2 | 4/2021 | Nawrocki et al. |
| 11,672,529 | B2 * | 6/2023 | Nawrocki ........ A61B 17/06166 606/228 |
| 2001/0044639 | A1 | 11/2001 | Levinson |
| 2003/0149447 | A1 | 8/2003 | Morency et al. |
| 2004/0122456 | A1 | 6/2004 | Saadat et al. |
| 2005/0004576 | A1 | 1/2005 | Benderev |
| 2005/0049635 | A1 | 3/2005 | Leiboff |
| 2007/0005109 | A1 | 1/2007 | Popadiuk et al. |
| 2007/0257395 | A1 | 11/2007 | Lindh et al. |
| 2008/0200751 | A1 | 8/2008 | Browning |
| 2008/0281357 | A1 | 11/2008 | Sung et al. |
| 2008/0312688 | A1 * | 12/2008 | Nawrocki ........ A61B 17/06166 606/228 |
| 2009/0018577 | A1 | 1/2009 | Leung et al. |
| 2009/0076547 | A1 | 3/2009 | Sugimoto et al. |
| 2009/0248067 | A1 | 10/2009 | Maiorino |
| 2009/0248070 | A1 | 10/2009 | Kosa et al. |
| 2009/0312791 | A1 | 12/2009 | Lindh, Sr. et al. |
| 2010/0084780 | A1 | 4/2010 | Lindh, Sr. et al. |
| 2010/0146770 | A1 * | 6/2010 | Morency .......... A61B 17/06166 29/557 |
| 2010/0211098 | A1 | 8/2010 | Hadba et al. |
| 2010/0274283 | A1 | 10/2010 | Kirsch et al. |
| 2010/0298871 | A1 * | 11/2010 | Ruff ....................... A61B 17/11 606/228 |
| 2011/0054522 | A1 | 3/2011 | Lindh, Sr. et al. |
| 2011/0093010 | A1 | 4/2011 | Genova et al. |
| 2011/0106152 | A1 | 5/2011 | Kozlowski |
| 2012/0016183 | A1 | 1/2012 | Gellman |
| 2012/0046525 | A1 | 2/2012 | Russell et al. |
| 2013/0059907 | A1 | 3/2013 | Hsieh et al. |
| 2013/0085525 | A1 | 4/2013 | Nawrocki et al. |
| 2013/0172944 | A1 | 7/2013 | Fritzinger et al. |
| 2014/0081321 | A1 | 3/2014 | Nawrocki et al. |
| 2019/0321028 | A1 | 10/2019 | Dinino et al. |

FOREIGN PATENT DOCUMENTS

| | | | |
|---|---|---|---|
| EP | 1867288 | B1 | 4/2010 |
| EP | 3412219 | A1 | 12/2018 |
| EP | 2895081 | B1 | 4/2019 |
| GB | 1091282 | A | 11/1967 |
| RU | 2400162 | C2 | 9/2010 |
| WO | 9506447 | A1 | 3/1995 |
| WO | 2004030704 | A2 | 4/2004 |
| WO | 2009020795 | A1 | 2/2009 |
| WO | 2010051506 | A1 | 5/2010 |
| WO | 2012071227 | A1 | 5/2012 |
| WO | 2013048947 | A1 | 4/2013 |
| WO | 2014043610 | A1 | 3/2014 |
| WO | 2019060365 | A1 | 3/2019 |

OTHER PUBLICATIONS

International Search Report and Written Opinion received for PCT Application No. PCT/US2012/056858, mailed on Nov. 29, 2012, 13 pages.

Invitation to Pay Additional Fees received for PCT Application No. PCT/US2013/059907, mailed on Nov. 28, 2013, 6 pages.

* cited by examiner

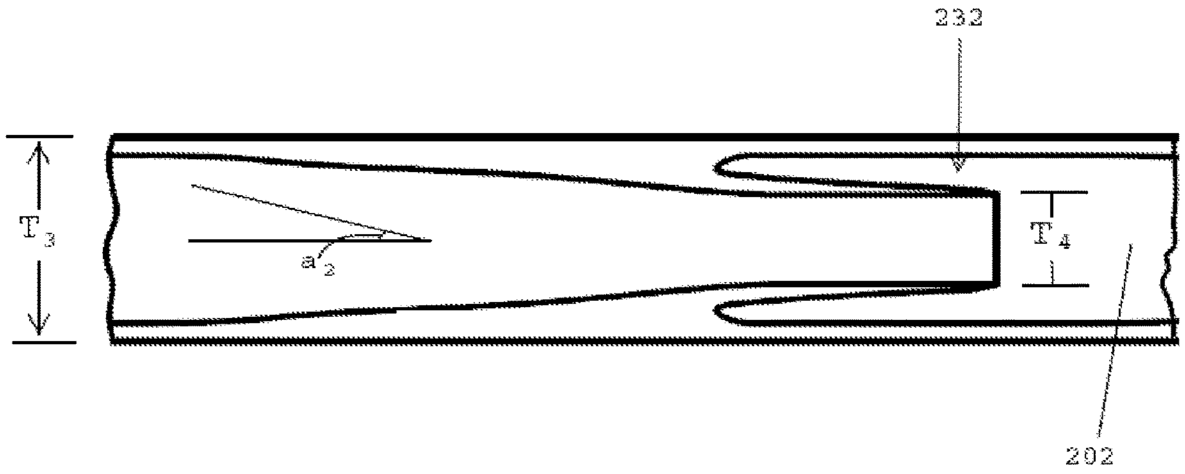
FIG. 13
FIG. 14
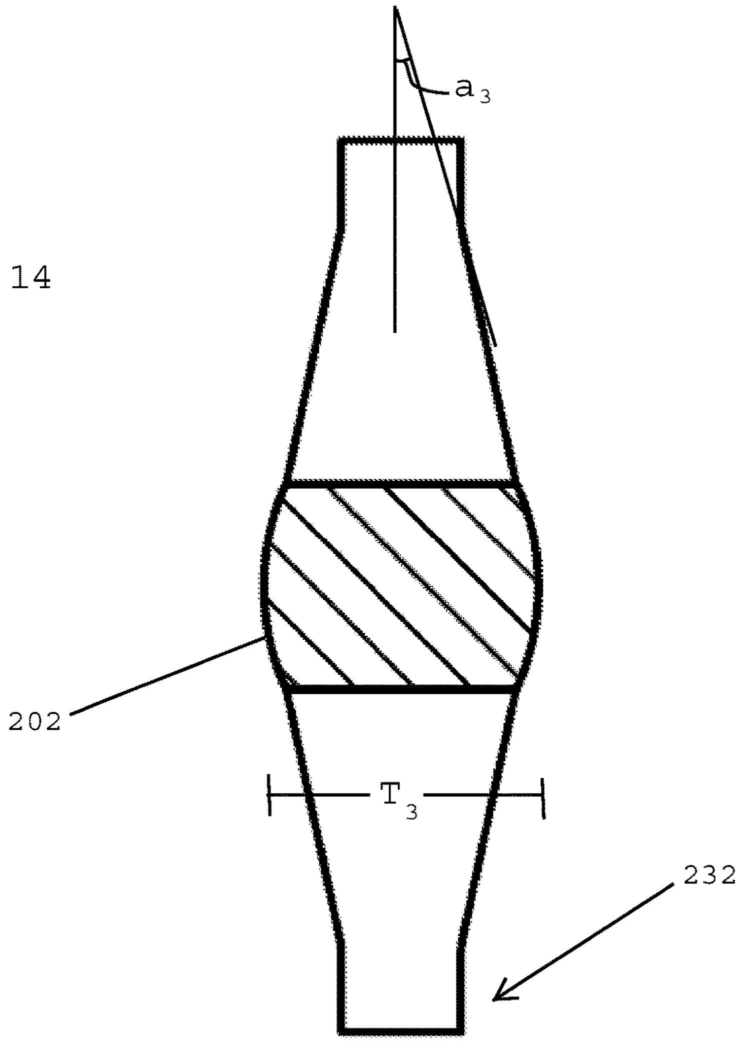

BARBED SUTURES HAVING CONTOURED BARBS THAT FACILITATE PASSAGE THROUGH TISSUE AND INCREASE HOLDING STRENGTH

CROSS-REFERENCE TO RELATED APPLICATIONS

The present application is a continuation of commonly assigned U.S. patent application Ser. No. 13/621,625, filed Sep. 17, 2012, the disclosure of which is hereby incorporated by reference herein.

BACKGROUND OF THE INVENTION

Field of the Invention

The present invention generally relates to the field of medical devices, and more particularly relates to barbed sutures having barbs that are specifically designed to facilitate passage through tissue when pulled in a first direction and that exhibit maximum holding strength when pulled in an opposite, second direction.

Description of the Related Art

Many wounds and surgical incisions are closed using surgical sutures or other forms of surgical closure devices. One type of surgical suture, commonly referred to a barbed suture, is well known and has recently gained attention for use in various medical applications. Typically, barbed sutures are constructed with a series of “barbs” or “protrusions” (used interchangeably herein) that extend outwardly from a central core or filament of the suture. The barbs function to increase the holding strength of the suture and/or eliminate the need for knot tying. The size and shape of the barbs have practical limitations in a surgical setting, and cannot simply be increased in size wherever increased holding strength is desired.

Some conventional sutures and barbed sutures have been known to include anchors, tabs or the like on the distal end of the suture to provide a “stop” at the distal end that increases the holding strength of the suture and that eliminates the need to tie knots to secure the suture. Conventional thinking dictates that the larger the surface area of the stop in a direction perpendicular to the direction of insertion of the suture, the more holding strength that will be achieved. Again, there are practical limitations on size, however, because large masses may be intolerable in surgical procedures and/or palpable and therefore undesirable. Further, with T-shaped stops, the perpendicular portion is structurally weak when a bending moment is applied as it would be when pulling on the suture to approximate a wound.

In view of the above-identified deficiencies, there remains a need for surgical sutures having enhanced holding strength without significantly increasing the insertion force, stiffness of the suture, or palpability of the device. There also remains a need for surgical sutures having barbs that are designed to allow the suture to pass easily through tissue when the suture is pulled in a first direction, but that exhibit maximum holding strength for holding the suture in place when the suture is pulled in an opposite, second direction.

SUMMARY OF THE INVENTION

The present invention provides a wound closure device including a filamentary element having a proximal end and a distal end, a stop element coupled to the distal end of the filamentary element and having a leading edge area defined by thickness and a width, and a total surface area. The leading edge area faces substantially perpendicular to a longitudinal axis of the filamentary element, and the ratio of the leading edge area to the total surface area is less than 10%. According to one embodiment, the ratio is less than 5%.

According to various embodiments, the width of the stop element may be greater than 70 mils, the length of the stop element may be greater than 70 mils, and/or the maximum thickness of said stop element may be between 6 and 25 mils.

According to one embodiment, the thickness of the stop element varies, and/or a minimum thickness of the stop element may be between 4 and 12 mils. According to yet another embodiment, the leading edge thickness includes a maximum thickness at a center and/or at first and/or second outer edges, and a minimum thickness at a location between the center and the first outer edge and between the center and the second outer edge.

In yet another embodiment, the wound closure device further includes a plurality of projections extending outwardly from the filamentary element along at least a portion of its length. The plurality of projections may extend outwardly from said filamentary element by approximately 6-25 mils.

The device may be made of a polymeric, metallic or ceramic material that are absorbable or non-absorbable. In yet another embodiment, the device is made of a polymer material selected from the group consisting of absorbable and non-absorbable homopolymers, random copolymers, block copolymers or blends made from polydioxanone, polyglactin, polyglycolic acid, copolymers of glycolide, lactide, and/or caprolactone, polyoxaesters, poliglecaprone, polypropylene, polyethylene, polyvinylidene fluoride (PVDF), hexafluoropropylene, copolymers of vinylidene fluoride and hexafluoropropylene, polyesters, polyethylene terephthalate, polybutylene terephthalate, glycol-modified polyethylene terephthalate, polytetrafluoroethylene, fluoropolymers, thermoplastic elastomers, ionomers, copolymers of ethylene and methacrylic acid, polyamides, polytetramethylene oxide, polystyrene, polybutadiene, polybutylene, etc. including combinations and/or copolymers of absorbable and non-absorbable materials.

According to yet another embodiment, a ratio of the length to maximum thickness of the stop element is greater than 4.

In yet another embodiment, the maximum thickness of the stop is approximately 8-25 mils, the width of the stop is approximately 70-120 mils, and the length of the stop is approximately 39-200 mils.

The present invention also provides a wound closure device including a filamentary element extending along a longitudinal axis between a proximal end and a distal end, and a stop element coupled to the distal end of the filamentary element and that has a length extending substantially parallel to the longitudinal axis of the filamentary element, a width extending substantially perpendicular to said longitudinal axis, and a maximum thickness. The ratio of the length to the maximum thickness of the stop element is at least 4.

In alternate embodiments, the maximum thickness of the stop element is between 8 and 25 mils, the length of the stop element is greater than 39 mils, and/or the width of the stop element is between 70 and 120 mils.

In yet another embodiment, the wound closure device further includes a plurality of projections extending outwardly from the filamentary element along at least a portion of its length.

In yet another embodiment, the thickness of the stop element varies, and in another particular embodiment, the leading edge thickness includes a maximum thickness at a center and/or at first and/or second outer edges, and a minimum thickness at a location between the center and the first outer edge and between the center and the second outer edge.

Also provided is a wound closure device including a filamentary element extending along a longitudinal axis between a proximal end and a distal end, and a stop element coupled to the distal end of the filamentary element. The stop element has a length extending substantially parallel to the longitudinal axis of the filamentary element, a width extending substantially perpendicular to the longitudinal axis, and a maximum thickness, and for any given maximum thickness of the stop element, the ratio of the length to the width of the stop element is at least 1.

In a further embodiment, the ratio of the length to the width of the stop element is at least 1.5.

In one embodiment, a wound closure device preferably includes a filamentary element having a proximal end and a distal end, and a plurality of barbs extending outwardly from the filamentary element. Each barb desirably has a base connected with the filamentary element, a tip spaced from the base, and an outer edge that extends between the base and the tip.

In one embodiment, the outer edge desirably includes a first section having a concave surface that extends between the base and a transition point of the barb and a second section having a convex surface that extends between the transition point of the barb and the tip of the barb. The outer edge preferably transforms from the concave surface of the first section to the convex curve of the second section at the transition point of the barb. In one embodiment, the concave surface of the first section of the barb has a radius of about 0.075-0.25 inches, and the convex surface of the second section of the barb has a radius of about 0.05-0.1 inches.

In one embodiment, at least one barb has a tip having a convexly curved surface facing the distal end of the filamentary element. The convexly curved outer surface desirably extends between the outer and inner edges of the barb and has a radius of about 0.003-0.006 inches.

In one embodiment, the filamentary element has a length and the barbs are evenly spaced along the length of the filamentary element. In one embodiment, the tips of the evenly spaced barbs define a tip-to-tip pitch of about 0.03-0.09 inches.

In one embodiment, the barbs include pairs of barbs evenly spaced along the length of the filamentary element. The barbs in each pair are desirably aligned with one another along the length of the filamentary element. In one embodiment, the barbs in each pair project away from one another and are disposed on opposite, lateral sides of the filamentary element. In one embodiment, the tips of the barbs in each pair define a lateral tip-to-tip distance of about 0.025-0.1 inches.

In one embodiment, each barb has the outer edge facing away from the filamentary element and an inner edge spaced from and facing the filamentary element. In one embodiment, at least one barb has an inner edge that extends between the barb base and the barb tip. In one embodiment, the barb includes an interior concave surface extending between the inner edge of the barb and the filamentary element having a radius of about 0.002-0.006 inches.

In one embodiment, at least one of the barbs extends along a longitudinal axis that defines an acute angle with the longitudinal axis of the filamentary element of about 5-60°.

In one embodiment, the bases of the barbs are thicker than the tips of the barbs. In one embodiment, the barbs taper inwardly between the base and the tip at an angle of about 1-20°.

In one embodiment, the wound closure device includes a stop element connected with the distal end of the filamentary element. The stop element has a total surface area and a leading edge area defined by a thickness and a width, whereby the leading edge area extends substantially perpendicular to the longitudinal axis of the filamentary element. In one embodiment, the ratio of the leading edge area to the total surface area is less than 10%.

In one embodiment, a wound closure device includes a filamentary element having a proximal end, a distal end, and a longitudinal axis extending between the proximal and distal ends, and a plurality of barbs extending outwardly from the filamentary element. In one embodiment, each barb has a base connected with the filamentary element, a tip spaced from the base, and an outer edge that extends between the base and the tip. The outer edge of the barb preferably includes a first section having a concave surface with a radius of about 0.075-0.25 inches that extends between the base and a transition point of the barb and a second section having a convex surface with a radius of about 0.05-0.1 inches that extends between the transition point of the barb and the tip of the barb. The barb tip desirably has a convex surface facing the distal end of the filamentary element having a radius of about 0.003-0.006 inches.

In one embodiment, the barbs are evenly spaced along the length of the filamentary element and define a longitudinal tip-to-tip pitch of about 0.03-0.09 inches. The plurality of barbs preferably includes pairs of barbs that are aligned with one another and evenly spaced along the length of the filamentary element. The barbs in each of the pairs preferably project away from one another and are disposed on opposite sides of the filamentary element, whereby the tips of the barbs in each pair define a lateral tip-to-tip distance of about 0.025-0.1 inches.

These and other objects, features and advantages of the present invention will be apparent from the following detailed description of illustrative embodiments thereof, which is to be read in connection with the accompanying drawings.

BRIEF DESCRIPTION OF THE DRAWINGS

FIG. 13 shows a top plan view of the section of the filamentary element having barbs shown in FIG. 12B.

FIG. 14 shows a cross-section view of the filamentary element having barbs taken along line FIG. 14-FIG. 14 of FIG. 12B.

DETAILED DESCRIPTION

Figure 1:
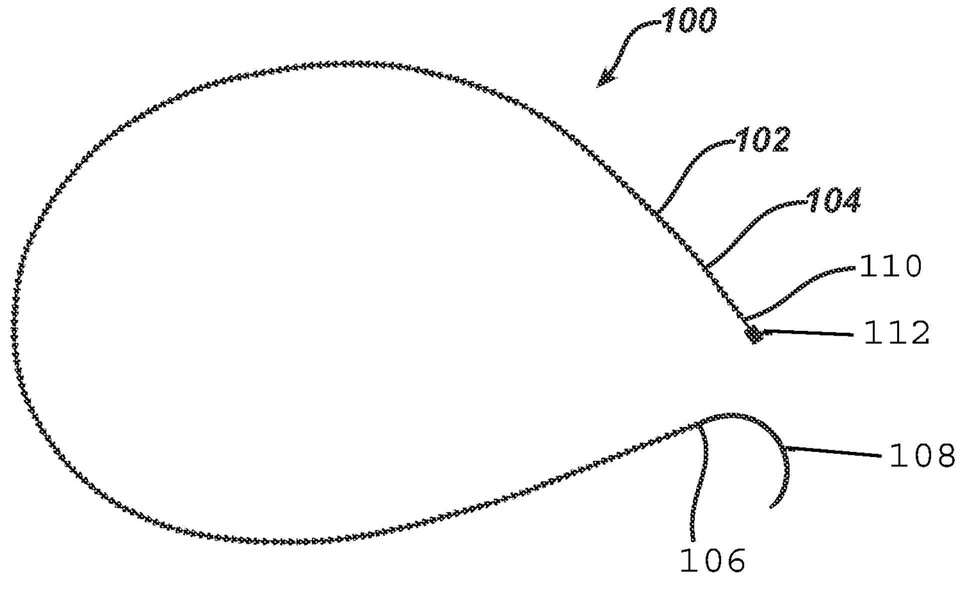
FIG. 1 shows a wound closure device including an insertion needle and a stop element, in accordance with one embodiment of the present invention.
Figure 2:
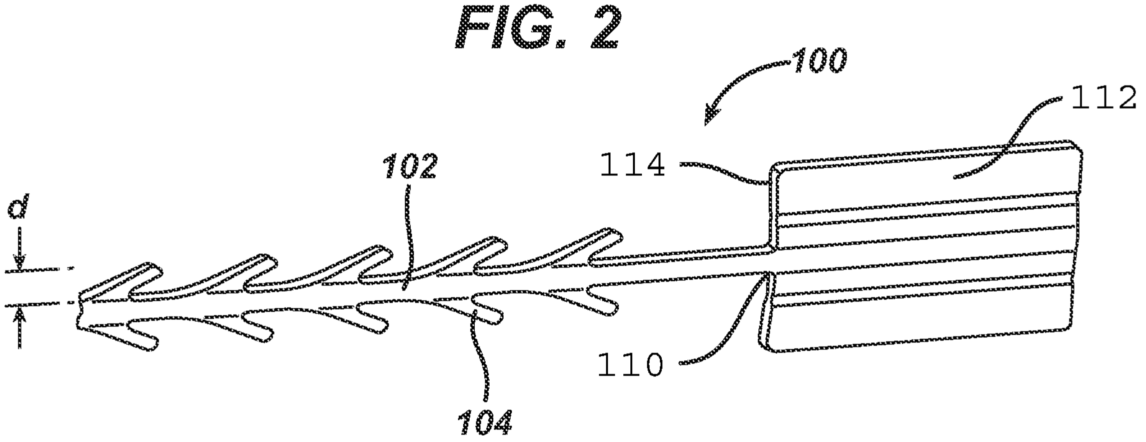
FIG. 2 is an enlarged view of the distal end of the wound closure device and the stop element of FIG. 1.
Figure 3:
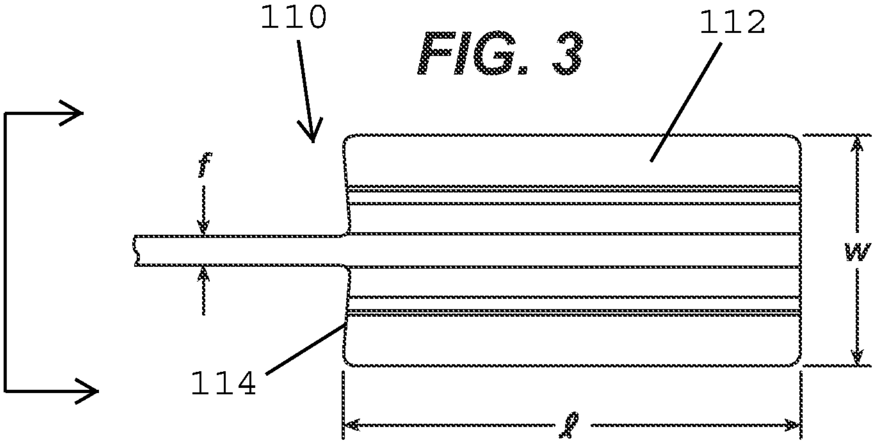
FIG. 3 is a top view of the stop element of the wound closure device of FIGS. 1 and 2.

FIG. 1 illustrates an exemplary embodiment of a wound closure device 100 according to the present invention. Referring to FIGS. 1 and 2, the wound closure device 100 includes a filamentary element 102 comprised of any suitable surgical suture material (i.e., absorbable and non-absorbable polymeric materials, metallic, or ceramic materials) that preferably includes a plurality of barbs 104 that extend outwardly therefrom. The suture may be formed by any suitable method, but preferably is compound profile punched from preformed material in a manner described in more detail in U.S. Patent Publication No. 2007/0257395, which is incorporated herein by reference in its entirety. Referring to FIG. 1, the proximal end 106 of the wound closure device may include a needle or other insertion device 108. Referring to FIGS. 1-5, in one embodiment, the distal end 110 of the wound closure device includes a fixation tab or stop element 112 or the like. The stop element 112 has a leading edge 114 defined by a leading edge thickness t (FIG. 5) and a leading edge width w (FIGS. 3 and 5). The stop element 112 also has a length l (FIG. 3). As indicated previously, known T-shaped configurations have relatively weak stiffness when a bending moment is applied, such as when tension is applied to the suture to approximate a wound. The graph depicted in FIG. 6 more clearly illustrates the advantage of the present invention over a T-shaped end configuration. Fixation tabs of equal leading edge maximum thickness (t) and width (w) (leading edge area), but varying length (I) were made and the holding strength tested. The holding strength was tested by passing the barbed suture through a porcine abdominal wall fascia sample and pulling against the fixation tab until failure occurred either by the stop breaking in some fashion, the stop pulling through the tissue, or a combination of both. The maximum load prior to failure was recorded and illustrated in FIG. 6.

Figure 6:
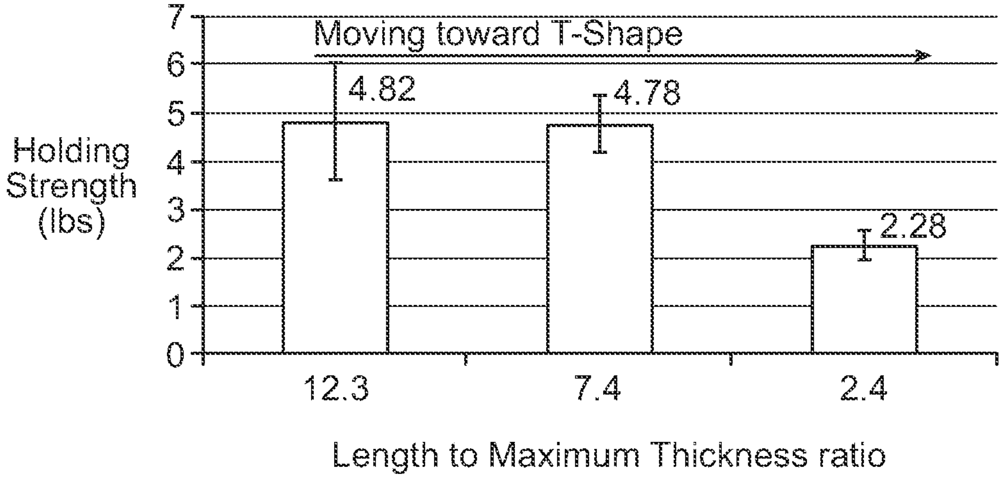
FIG. 6 is a graph illustrating the holding strength of fixation tabs of equal leading edge maximum thickness and width, but with varying length.

As shown in the FIG. 6 graph, the holding strength decreases as the geometry becomes more like a T-shaped member, or in other words, as the ratio of length to leading edge area or length to maximum thickness decreases. The holding strength can be increased by increasing the thickness or width of the stop, but as indicated previously, there are practical and clinical limitations on the size and mass that can be implanted.

Figure 7:
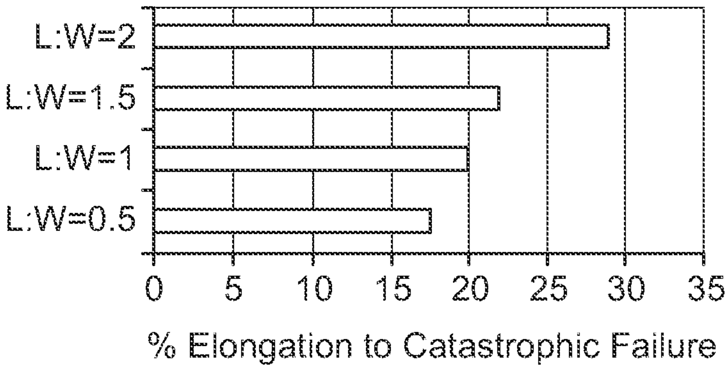
FIG. 7 is a graph illustrating elongation of a fixation tab as a function of length to width ratio for a given maximum thickness.

In addition to the length to maximum thickness or leading edge area ratio, the length l to width w ratio is also a significant consideration for any given maximum thickness. Surprisingly and counter-intuitively, a ratio of at least 1:1 provides much increased holding strength. FIG. 7 illustrates the elongation of the fixation stop or tab as a function of the length to width ratio for a given maximum thickness. As shown, the percentage of elongation (or more simply the amount of deformation) required to reach catastrophic failure increases with increasing length to width ratio.

Figure 8:
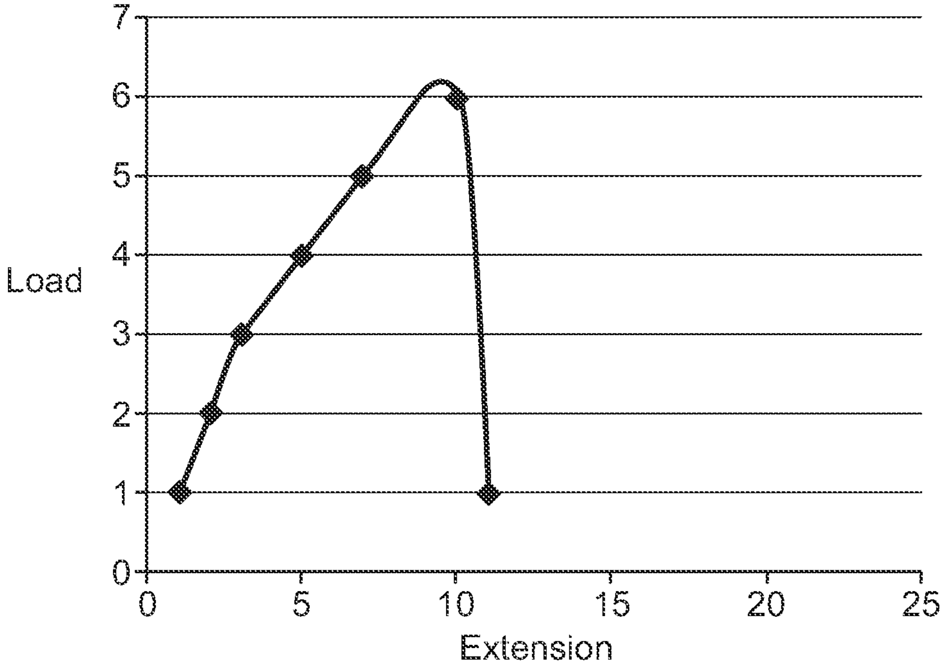
FIG. 8 is a graph illustrating a load-extension curve for a fixation tab length to width ratio of 0.5.
Figure 9:
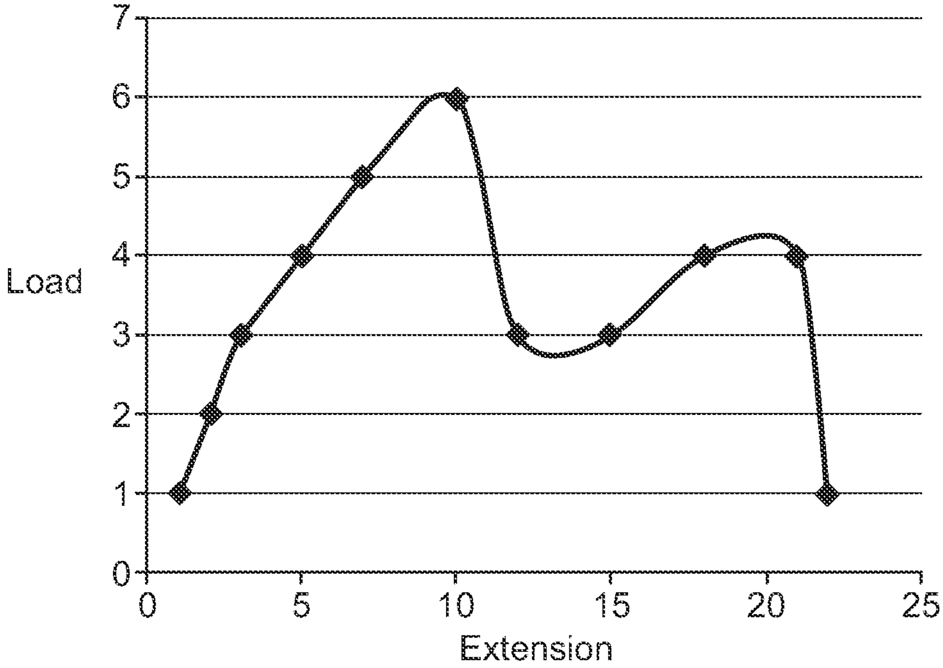
FIG. 9 is a graph illustrating a load-extension curve for a fixation tab length to width ratio of 2.

In addition to raw elongation percentages, the actual amount of energy required for the failure of the device increases with increasing length to width ratios. This is illustrated by FIGS. 8 and 9, in which the area under the load-extension curve is a measure of the strain energy until catastrophic failure. As the length to width ratio increases, the amount of strain energy required to reach catastrophic failure significantly increases. FIG. 8 illustrates a load-extension curve for a fixation tab having a length to width ratio of 0.5:1. As illustrated, the device reaches a peak load then decreases dramatically with sudden failure. FIG. 9 illustrates a load-extension curve for a fixation tab having a length to width ratio of 2:1. As illustrated, the curve has a second peak, and much greater extension before catastrophic failure occurs. In other words, the strain energy significantly increases as the length to width ratio increases from 0.5 to 2.

Figure 4:
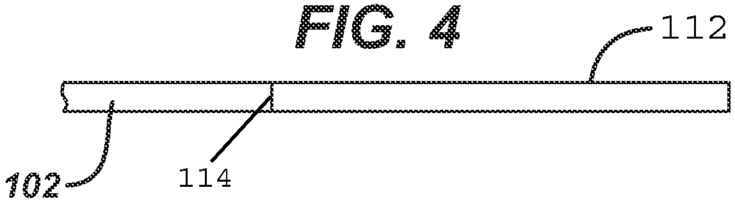
FIG. 4 is a side view of the stop element of the wound closure device of FIGS. 1-3.
Figure 5:
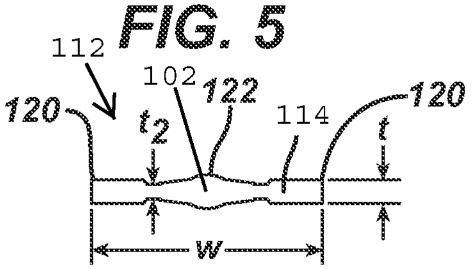
FIG. 5 is a cross-sectional view of the stop element of the wound closure device of FIG. 3 taken along line FIG. 5-FIG. 5 thereof.

Referring to FIGS. 3-5, the leading edge 114 of the stop element 112 has relatively little surface area in contact with tissue when the suture is under tension, but its ratio of length l to maximum thickness t is very large. Thus, the actual area in contact with tissue (i.e., the area of the leading edge area 114) in the direction of load is very small relative to the overall dimensions of the stop element 112. This relatively long length, but minimal thickness allows the stop to be placed in the wound in a relatively flat position, which minimizes palpability and allows the opposing sides of the tissue to neatly cover the stop. Since the stop lies nicely in the tissue, it can be placed at the apex of the wound, lateral to one side of the wound etc, without impeding the surgeon's individual closure technique.

In a preferred embodiment, the leading edge 114 relative to the total surface area of the stop 112 (sum of surface area of all sides) is small, preferably less than 10% and more preferably less than 5%. This is counterintuitive, as conventional thinking dictates that in order to increase holding strength and/or minimize failure, one must increase or maximize the surface area under load in order to spread out the load and decrease the load per unit area. The relatively long length l, but minimal thickness t results in clinical advantages, including flat positioning that minimizes palpability, and versatile positioning as mentioned above.

According to one preferred embodiment, shown in detail in the cross-sectional view of FIG. 5, the leading edge 114 of the stop element 112 is preferably not rectangular, but rather has a thickness that varies across its width. In one embodiment, the stop element 112 has a maximum thickness t at its outer edges 120 and center 122, and a minimum thickness $t_2$ at points between the center and outer edges. In this embodiment, the filamentary element 102 has a filament width f of approximately 5-25 mils, and the barbs 104 extend outwardly therefrom by a distance d (FIG. 2) of approximately 6-25 mils. Referring to FIG. 3, the stop 112 has a length l of at least 39 mils, preferably 100 to 200 mils, and a width of greater than 70 mils, more preferably greater than 90 mils, and most preferably greater than 95 mils. Further, referring to FIGS. 3-5, the maximum thickness t is greater than 6 mils, and preferably between 10 and 25 mils, and the minimum thickness $t_2$ is less than 15 mils, but preferably between approximately 5 and 9 mils. In one embodiment, the length to maximum thickness ratio is preferably greater than 4, and the length to minimum thickness is preferably greater than 9. In one embodiment, the length to width ratio is preferably greater than 1, and more preferably greater than 1.5.

Figure 10:
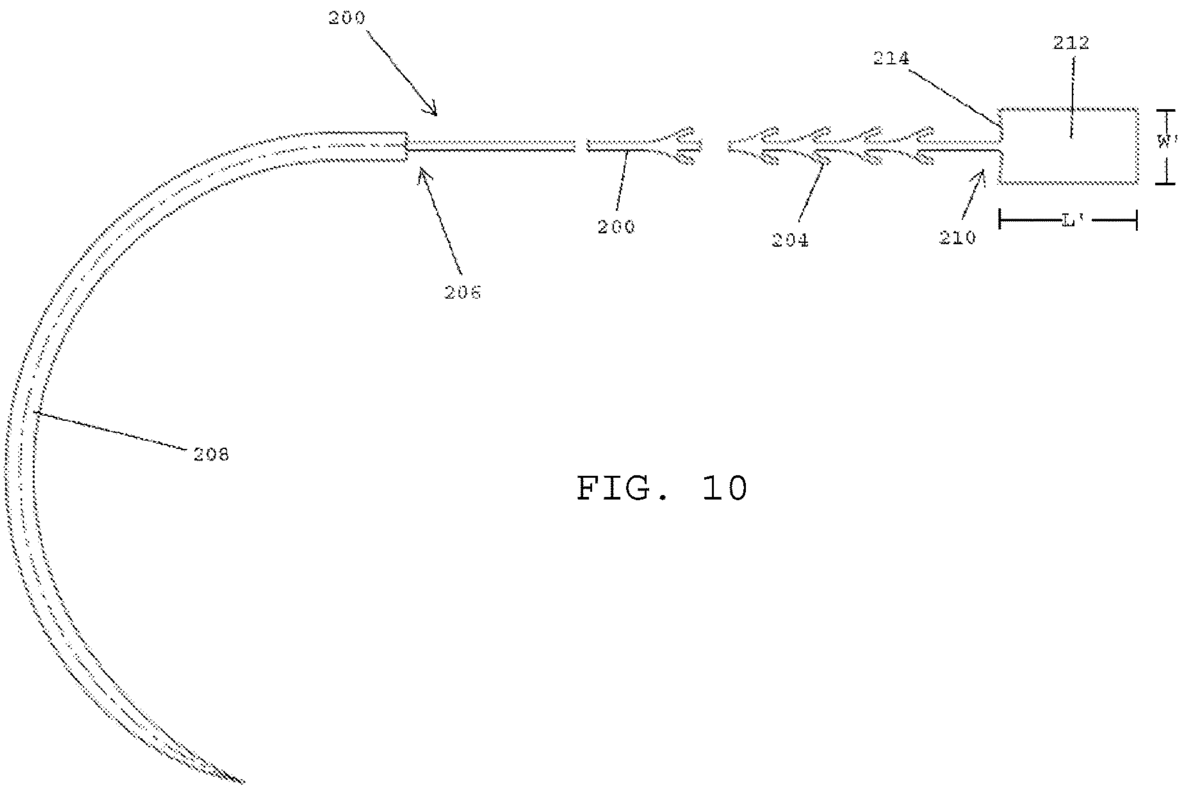
FIG. 10 illustrates a wound closure device including a filamentary element having barbs, an insertion needle connected with a leading end of the filamentary element, and a stop element connected with a trailing end of the filamentary element, in accordance one embodiment of the present invention.

Referring to FIG. 10, in one embodiment, a wound closure device 200 preferably includes a filamentary element 202 having barbs 204 that extend outwardly therefrom. The filamentary element 202 desirably includes a proximal end 206, an insertion needle 208 connected with the proximal end 206 of the filamentary element 202, a distal end 210 of the filamentary element 202 that is remote from the proximal end 206 of the filamentary element 202, and a stop 212 connected with the distal end 210 of the filamentary element 202. The stop element 212 has a leading edge 214 having a leading edge thickness (not shown) and a leading edge width W'. The stop element 212 also has a length L'.

Figure 11:
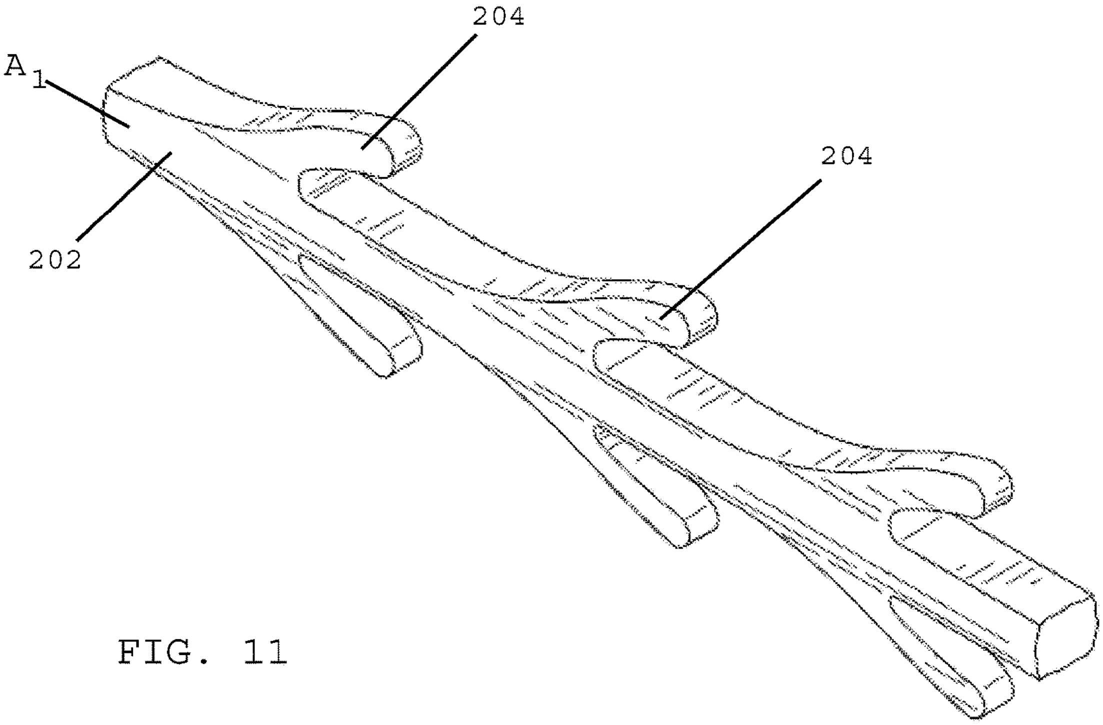
FIG. 11 shows a perspective view of a section of the filamentary element having barbs shown in FIG. 10.
Figure 12A:
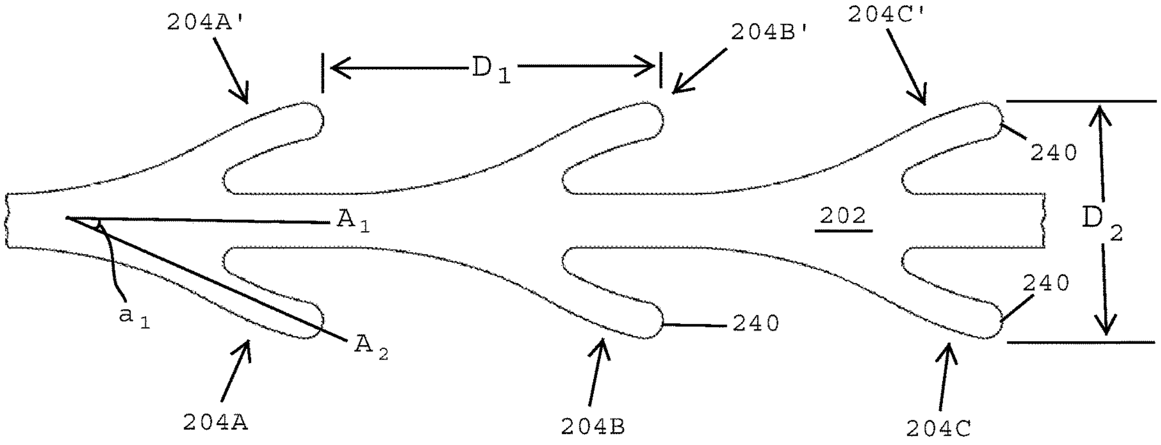
FIG. 12A shows a left side view of the section of the filamentary element having barbs shown in FIG. 11.
Figure 12B:
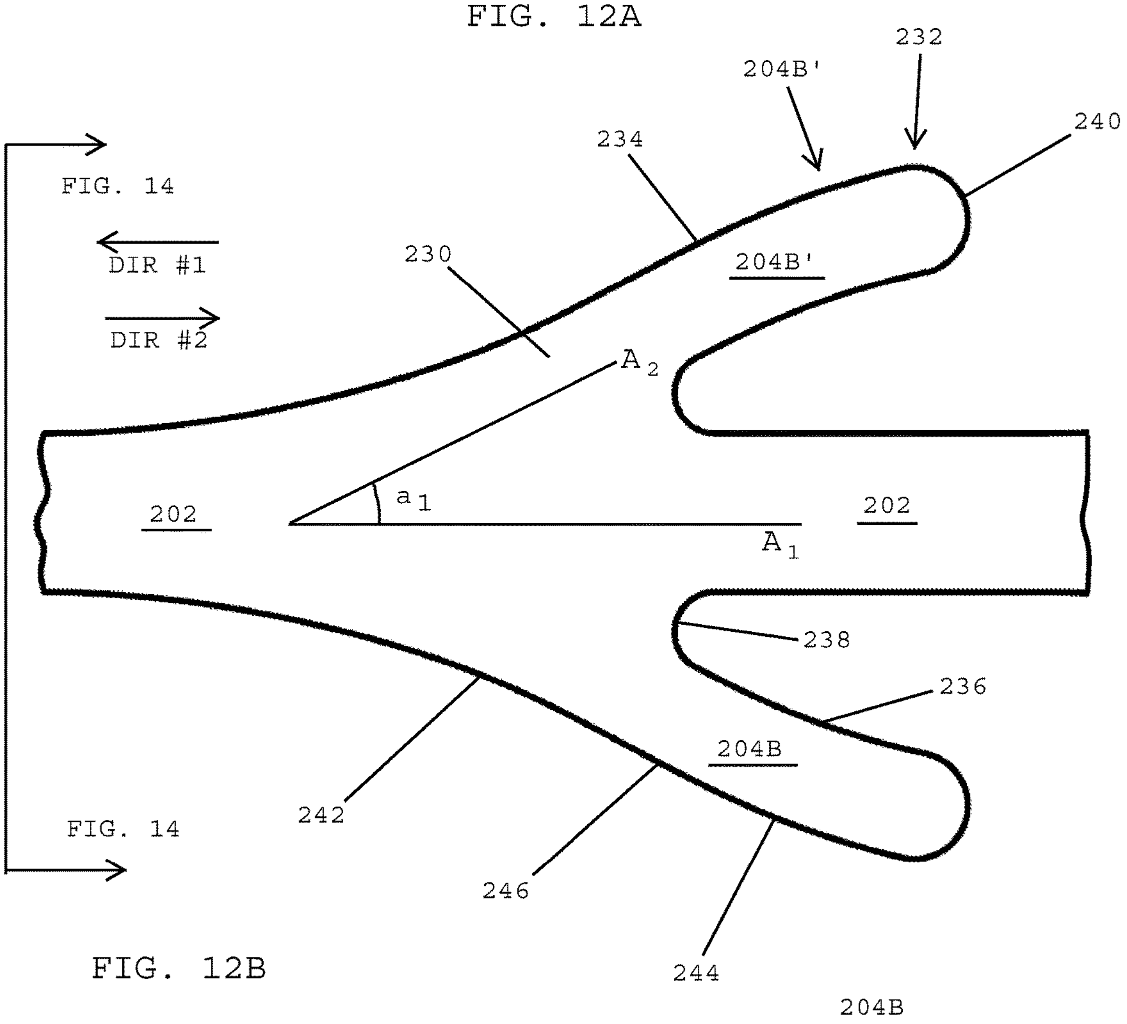
FIG. 12B shows a magnified view of the section of the filamentary element having barbs shown in FIG. 12A.

Referring to FIG. 11, in one embodiment, the filamentary element 202 has a plurality of barbs 204 extending outwardly from the filamentary element. Referring to FIGS. 12A and 12B, in one embodiment, the barbs 204 of the filamentary element 202 are evenly spaced from one another along the length of the filamentary element 202 (i.e., along the longitudinal axis $A_1$). In one embodiment, the filamentary element 202 has the longitudinal axis $A_1$ and the barbs 204 extend along an axis $A_2$ that defines an angle $\alpha_1$ with the longitudinal axis $A_1$. In one embodiment, the angle $\alpha_1$ is about 5-60°, and more preferably about 10-49°. The exact size of the angle $\alpha_1$ is desirably selected to control the flexibility of the barbs 204 during tissue passage and also establish the barb holding strength after the wound closure device 200 has been implanted in tissue.

In one embodiment, the barbs are aligned in pairs that extend away from one another on opposite sides of the filamentary element 202. FIG. 12A shows three different pairs of barbs that are aligned with one another along the length of the filamentary element 202 including a first pair of barbs 204A, 204A', a second pair of barbs 204B, 204B', and a third pair of barbs 204C, 204C'. Only three pairs of barbs are shown in FIG. 12A because only a small section of the filamentary element 202 is illustrated. In other embodiments, however, a filamentary element 202 may include 50, 100, 150 or more pairs of barbs that are aligned with one another along the length of the filamentary element and that extend away from one another on opposite sides of the filamentary element. In one embodiment, at least some of the barbs extending from opposite sides of the filamentary element are staggered relative to one another.

Referring to FIGS. 12A and 12B, in one embodiment, each barb 204 includes a base 230 that is connected with the filamentary element 202, a tip 232 that is spaced from the base 230, an outer edge 234 that extends between the base 230 and the tip 232, and an inner edge 236 that extends between the base 230 and the tip 232. The outer edge 234 of the barb 204 preferably faces away from the filamentary element 202 and the inner edge 236 of the barb preferably faces toward the filamentary element 202. Each barb 204 also desirably includes an interior curved surface 238 that extends between the inner edge 236 of the barb 204 and the filamentary element 202.

Referring to FIG. 12A, in one embodiment, the distance between tips 232 of adjacent barbs 204 that are spaced from one another along the longitudinal axis $A_1$ of the filamentary element 202 defines a barb pitch $D_1$ of about 0.03-0.09 inches, and more preferably about 0.075 inches. In one embodiment, the barb pitch $D_1$ is consistent for all of the barbs so that the barbs are evenly spaced from one another along the length of the filamentary element. The barb pitch $D_1$ between the adjacent tips 232 is selected to control passage of the filamentary element 202 through tissue and improves the holding strength of the wound closure device 200. If the barb pitch $D_1$ between adjacent barb tips is too great (i.e., over 0.09 inches), then the holding strength of the wound closure device decreases. If the barb pitch $D_1$ between adjacent barb tips is too small (i.e., less than about 0.03 inches), then the force required to pass the wound closure device 200 through tissue increases to undesirable levels.

Referring to FIG. 12A, in one embodiment, the lateral tip-to-tip distance $D_2$ between the barbs of a pair of barbs (e.g. barbs 204C and 204C') is about 0.025-0.1 inches, and more preferably about 0.03-0.06 inches. The lateral tip-to-tip distance $D_2$ preferably controls passage of the wound closure device 200 through tissue and enhances holding strength of the wound closure device. If the lateral tip-to-tip distance $D_2$ is too small (i.e., less than 0.025 inches), then the holding strength of the wound closure device 200 decreases to undesirable levels. If the lateral tip-to-tip distance $D_2$ is too large (greater than 0.1 inches), then the force required to pass the wound closure device 200 through tissue increases to undesirable levels.

Referring to FIGS. 12A and 12B, in one embodiment, the tips 232 of the barbs 204 define a convex radial surface 240 having a radius of about 0.003-0.006 inches, and more preferably about 0.004 inches. For each barb, the convex radial surface 240 of the tip 232 desirably helps control the flexibility of the barb 204 during tissue passage and helps dictate the moment arm for the barb 204, thereby minimizing the likelihood of the barb bending backwards once implanted in tissue.

Referring to FIG. 12B, in one embodiment, the outer edge 234 of each barb 204 includes a first section 242 defining a concave surface and a second section 244 defining a convex surface. The first section 242 with the concave surface extends between the base 230 and a transition point 246 of the barb 204. The second section 244 with the convex surface extends between the transition point 246 of the barb 204 and the tip 232 of the barb 204. In one embodiment, the concave surface of the first section 242 has a radius of about 0.075-0.25 inches, and more preferably about 0.09-0.2 inches. The concave surface of the first section 242 preferably controls the flexibility of the barb 204 and passage of the wound closure device through tissue. The concave surface of the first section 242 defines the moment arm for the barb 204, which desirably minimizes the likelihood of the barb 204 bending backwards once implanted in tissue.

In one embodiment, the convex surface of the second section 244 of the barb has a radius of about 0.05-0.1 inches, and more preferably about 0.07 inches. The convex surface of the second section 244 preferably defines the moment arm of the barb, helps control the flexibility of the barb, and facilitates passage of the barb and the wound closure device 200 through tissue.

Referring to FIG. 12B, in one embodiment, one or more of the barbs 204 have a unique shape that desirably enables the barbs to more readily collapse inwardly toward the filamentary element 202 when the barbed suture is pulled through tissue in a first direction designated DIR #1, thereby minimizing the amount of force required to pull the barbed suture through tissue in the first direction DIR #1. In particular, the first section 242 of the outer edge of the barb 204 having a concave shape minimizes the profile of the barb relative to the tissue, which minimizes the amount of force required to pull the barbed suture through the tissue in the first direction DIR #1. In addition, the convex curve of the second section 244 of the barb, located between the transition point 246 of the barb and the tip 232 of the barb, minimizes the resistance level of the barb to inward flexing when the suture is pulled in the first direction DIR #1 so that the resistance level is significantly less than the level that would exist if second section 244 were a straight or concave surface. Thus, the unique shape of the outer edge 234 of each barb 204, having a first section 242 with a concave surface and a second section 244 with a convex surface minimizes the level of resistance provided by the barbed suture as the suture in pulled through tissue in the first direction DIR #1 and enables the barbs to more easily collapse inwardly toward the filamentary element 203. In one embodiment, the location of the transition point may be moved and the radii varied to change the moment arm of the barbs, which will change the ease of passage in the first direction and also change the resistance to movement in the second direction.

In one embodiment, a barbed suture includes one or more barbs 204 having a unique shape that desirably enables the barbs to more readily resist being bent toward the proximal end of the filamentary element 202 (backward bending) when the barbed suture is pulled through tissue in a second direction designated DIR #2, thereby maximizing the amount of force required to pull the barbed suture through tissue in the second direction DIR #2. In one embodiment, the concave surface of the first section 242 of the barb, located on the outer edge 234 of the barb 204, enables the barb to more easily flex away (i.e., bend backward) from the filamentary element 202 when the suture is pulled in the second direction DIR #2, thereby increasing the lateral tip-to-tip distance $D_2$ (FIG. 12A) between the respective tips 232 of the paired barbs 204B, 204B', which increases the resistance to movement of the suture in the second direction DIR #2. In addition, the convexly curved surface 240 at the tip 232 of the barb 204 provides more surface area at the tip for contacting the surrounding tissue when the barbed suture is pulled in the direction DIR #2, for further resisting movement of the barbed suture in the second direction DIR #2. Providing a tip 232 with a convex surface 240 provides more surface area for engaging tissue, and provides a dramatic improvement over tips having acutely angled surfaces that have less surface area for engaging tissue. In one embodiment, providing tips 232 having convex surfaces 240 minimizes the chance of the barbs causing tissue damage because the tips do not have sharp edges.

In one embodiment, the interior concave surface 238 of the barb 204 has a radius of about 0.002-0.006 inches, and more preferably about 0.003 inches. The selected radius of the interior concave surface 238 preferably helps control flexibility of the barb during tissue passage and helps dictate the moment arm of the barb for preventing the barbs from bending backwards once implanted.

Referring to FIGS. 13 and 14, in one embodiment, the filamentary element 202 of the wound closure device 200 has a greater thickness $T_3$ than the thickness $T_4$ of the tips 232 of the barbs 204. As a result, the wound closure device 200 is preferably thinner at the tips 232 of the barbs 204 than at the center of the filamentary element 202. As a result, the barbs 204 taper inwardly from the thickness $T_3$ of the center of the filamentary element 202 to the tips 232 by an angle $\alpha_2$ of about 1-20°, and more preferably about 2-10°. The taper of the barbs between the filamentary element 202 and the tip 232 helps control the flexibility of the barbs 204 during tissue passage and also helps dictate the holding strength of the barbs once the wound closure device 200 has been implanted in tissue.

While the foregoing is directed to embodiments of the present invention, other and further embodiments of the invention may be devised without departing from the basic scope thereof. As such, it is to be understood that the invention is not limited to the precise embodiments disclosed herein, that various other changes and modifications may be effected herein by one skilled in the art without departing from the scope or spirit of the invention, and that the scope of the present invention is to be limited only as set forth in the appended claims.

What is claimed is:

1. A wound closure device, comprising:

a filamentary element extending along a longitudinal axis from a proximal end to a distal end;

a plurality of barbs extending outwardly from the filamentary element, a first one of the barbs extending from a base connected to the filamentary element to a tip spaced distally from the base and facing the distal end of the filamentary element, an outer edge of the first barb extending from a proximal end of the base of the first barb to the tip of the first barb and facing away from the filamentary element, and an inner edge of the first barb extending from a distal end of the base of the first barb and facing toward the filamentary element, wherein the outer edge of the first barb includes a first section having a concave surface that extends between the base of the first barb and a first transition point and a second section having a convex curved surface that extends from the first transition point to a distal-most portion of the tip of the first barb, and wherein the inner edge of the first barb has a concave surface that extends to the tip of the first barb, a second one of the barbs that is adjacent and distal to the first barb extending outwardly from a same side of the filamentary element as the first barb and wherein the tip of the first barb and a tip of the second barb face the distal end of the filamentary element, the filamentary element having an outer surface that extends distally from the distal end of the base of the first barb to a proximal end of a base of the second barb;

a needle secured to the proximal end of the filamentary element; and a stop element extending distally from and fixed to the filamentary element distal of a distal-most one of the barbs, the stop element being adapted to resist movement of the wound closure device proximally through tissue within which the wound closure device has been embedded, wherein the stop element is a substantially planar element having a proximally facing leading edge, wherein a width of the leading edge in a direction perpendicular to the longitudinal axis of the filamentary element and parallel to a plane of the stop element is greater than a thickness of the leading edge in the direction perpendicular to the longitudinal axis of the filamentary element and perpendicular to the plane of the stop element.

2. The device of claim 1, wherein the stop element has a length along the longitudinal axis of the filamentary element that is greater than the width of the stop element.

3. The device of claim 1, wherein the tip of the first barb has a convex curved radial surface that extends from the second section of the outer edge of the first barb to the inner edge of the first barb, the convex curved radial surface of the tip of the first barb having a greater degree of curvature than the convex surface of the outer edge of the first barb.

4. The device of claim 1, further comprising a plurality of further barbs, the first and second barbs and the further barbs being evenly spaced from one another along a length of the filamentary element.

5. The device of claim 4, wherein each of the further barbs extends from a base connected to the filamentary element to a tip spaced distally from the base and facing the distal end of the filamentary element, an outer edge of each of the further barbs extending from a proximal end of its base to its tip and facing away from the filamentary element, and an inner edge of each of the further barbs extending from a distal end of its base and facing toward the filamentary element, wherein the outer edge of each of the further barbs includes a first section having a concave surface that extends between its base and a first transition point and a second section having a convex curved surface that extends from the first transition point to a distal-most portion of its tip, and wherein the inner edge of each one of the further barbs has a concave surface that extends to its tip.

6. The device of claim 4, wherein the tips of the plurality of barbs and the plurality of further barbs define a tip-to-tip pitch of from 0.03 to 0.09 inches.

7. The device of claim 4, wherein the plurality of barbs and the plurality of further barbs include pairs of barbs evenly spaced along the length of the filamentary element and wherein, the barbs of each pair of barbs are aligned with one another along the length of the filamentary element and extend away from the filamentary element in opposite directions.

8. The device of claim 7, wherein the tips of the plurality of barbs and the plurality of further barbs in each pair of barbs define a lateral tip-to-tip distance of from 0.025 to 0.1 inches.

9. The device of claim 1, wherein at least one of the barbs extends along a barb longitudinal axis that extends an acute angle relative to the longitudinal axis of the filamentary element.

10. The device of claim 9, wherein the acute angle between the barb longitudinal axis and the longitudinal axis of the filamentary element is from 5 to 60°.

11. The device of claim 1, wherein the first barb is defined by two walls that define a thickness of the first barb and wherein the walls of the first barb taper inwardly between the base and the tip of the first barb at an angle of from 1 to 20°.

12. A wound closure device, comprising:

a filamentary element extending along a longitudinal axis from a proximal end to a distal end;

a plurality of barbs extending outwardly from the filamentary element, a first one of the barbs extending from the filamentary element to a tip facing the distal end of the filamentary element, an outer edge of the first barb extending from the filamentary element to the tip of the first barb and facing away from filamentary element, and an inner edge of the first barb extending from a portion of the filamentary element distal of a first connection point at which the outer edge of the first barb meets the filamentary element, the inner edge of the first barb facing the filamentary element and forming a first concave surface that extends to the tip of the first barb, wherein the outer edge of the first barb includes a first section having a concave surface that extends between the first connection point and a first transition point and a second section having a convex curved surface that extends from the first transition point to a distal-most portion of the tip of the first barb, a second one of the barbs that is adjacent and distal to the first barb extending outwardly from a same side of the filamentary element as the first barb;

a needle secured to the proximal end of the filamentary element; and a stop element extending distally from and fixed to the filamentary element distal of a distal-most one of the barbs, the stop element being adapted to resist movement of the wound closure device through tissue within which the wound closure device has been embedded, wherein the stop element is substantially planar and has a proximally facing leading edge, a width of the leading edge in a direction perpendicular to the longitudinal axis of the filamentary element and parallel to a plane of the stop element being greater than a thickness of the leading edge in the direction perpendicular to the longitudinal axis of the filamentary element and perpendicular to the plane of the stop element.

13. The device of claim 12, wherein the plurality of barbs are evenly spaced along the filamentary element and tips of the plurality of barbs define a longitudinal tip-to-tip pitch of 0.03-0.09 inches, and wherein the barbs are formed in pairs, each pair of barbs including two barbs aligned with one another and along a length of the filamentary element, the barbs in each pair of barbs projecting away from the filamentary element in opposite directions and extending from opposite sides of the filamentary element.

14. The device of claim 13, wherein the tips of the plurality of barbs in each pair of barbs have convex curved radial surfaces and define a lateral tip-to-tip distance of 0.025-0.1 inches.

15. The device of claim 14, wherein a ratio of a first area of the leading edge of the stop element to a second area of a total surface of the stop element is less than 5%.

* * * * *